US009675725B2

(12) United States Patent
Worrilow

(10) Patent No.: US 9,675,725 B2
(45) Date of Patent: Jun. 13, 2017

(54) PURIFIED AIR AND METHODS OF MAKING AND USING THE SAME

(71) Applicant: LifeAire Systems, LLC, Allentown, PA (US)

(72) Inventor: Kathryn C. Worrilow, Fogelsville, PA (US)

(73) Assignee: LifeAire Systems, LLC, Allentown, PA (US)

( * ) Notice: Subject to any disclaimer, the term of this patent is extended or adjusted under 35 U.S.C. 154(b) by 0 days.

(21) Appl. No.: 14/837,849

(22) Filed: Aug. 27, 2015

(65) Prior Publication Data

US 2015/0367017 A1 Dec. 24, 2015

Related U.S. Application Data

(60) Division of application No. 13/554,366, filed on Jul. 20, 2012, now abandoned, which is a continuation-in-part of application No. 13/244,973, filed on Sep. 26, 2011, now Pat. No. 8,252,100, which is a continuation of application No. 12/732,246, filed on Mar. 26, 2010, now Pat. No. 8,252,099.

(51) Int. Cl.

| | |
|---|---|
| A61B 17/43 | (2006.01) |
| A61L 9/20 | (2006.01) |
| B01D 53/04 | (2006.01) |
| B01D 46/00 | (2006.01) |
| B01D 46/52 | (2006.01) |
| B01D 53/00 | (2006.01) |
| B01D 53/02 | (2006.01) |
| B01J 20/20 | (2006.01) |
| F24F 11/00 | (2006.01) |
| B01J 20/04 | (2006.01) |
| B01J 20/28 | (2006.01) |
| B01J 20/02 | (2006.01) |
| F24F 3/16 | (2006.01) |
| F24F 5/00 | (2006.01) |

(52) U.S. Cl.
CPC ............... *A61L 9/20* (2013.01); *A61B 17/43* (2013.01); *B01D 46/0028* (2013.01); *B01D 46/0036* (2013.01); *B01D 46/521* (2013.01); *B01D 53/007* (2013.01); *B01D 53/02* (2013.01); *B01D 53/04* (2013.01); *B01J 20/0222* (2013.01); *B01J 20/04* (2013.01); *B01J 20/20* (2013.01); *B01J 20/28052* (2013.01); *F24F 3/16* (2013.01); *F24F 11/0008* (2013.01); *A61L 2209/14* (2013.01); *A61L 2209/16* (2013.01); *B01D 2253/102* (2013.01); *B01D 2253/112* (2013.01); *B01D 2255/2073* (2013.01); *B01D 2257/708* (2013.01); *B01D 2257/91* (2013.01); *B01D 2259/4508* (2013.01); *B01D 2259/4533* (2013.01); *B01D 2259/804* (2013.01); *B01D 2267/40* (2013.01); *B01J 2220/42* (2013.01); *F24F 5/0089* (2013.01); *F24F 11/0012* (2013.01); *F24F 11/0015* (2013.01); *F24F 2003/1625* (2013.01); *F24F 2003/1667* (2013.01); *F24F 2011/0032* (2013.01); *Y02B 30/78* (2013.01)

(58) Field of Classification Search
CPC .................................. A61B 17/43; A61L 9/20
See application file for complete search history.

(56) References Cited

U.S. PATENT DOCUMENTS

| | | |
|---|---|---|
| 3,744,216 A | 7/1973 | Halloran |
| 3,804,942 A | 4/1974 | Kato et al. |
| 4,737,173 A | 4/1988 | Kudirka et al. |
| 5,129,928 A | 7/1992 | Chan et al. |
| 5,316,560 A | 5/1994 | Krone-Schmidt et al. |
| 5,330,722 A | 7/1994 | Pick et al. |
| 5,358,443 A | 10/1994 | Mitchell et al. |
| 5,632,954 A | 5/1997 | Coellner et al. |
| 5,772,738 A | 6/1998 | Muraoka |
| 5,833,740 A | 11/1998 | Brais |
| 5,858,041 A | 1/1999 | Luetkemeyer |
| 6,013,119 A | 1/2000 | Cecchi et al. |
| 6,156,089 A | 12/2000 | Stemmer et al. |
| 6,200,362 B1 | 3/2001 | Cecchi et al. |
| 6,225,110 B1 | 5/2001 | Cecchi et al. |
| 6,248,235 B1 | 6/2001 | Scott |
| 6,261,449 B1 | 7/2001 | Scott |
| 6,274,049 B1 | 8/2001 | Scott |
| 6,330,947 B1 | 12/2001 | Scott |
| 6,402,811 B1 | 6/2002 | Shanks et al. |
| 6,464,760 B1 | 10/2002 | Sham et al. |
| 6,508,367 B2 | 1/2003 | Scott |
| 6,524,457 B1 | 2/2003 | Scott |
| 6,623,544 B1 | 9/2003 | Kaura |
| 6,797,042 B2 | 9/2004 | LaFerriere et al. |

(Continued)

FOREIGN PATENT DOCUMENTS

| | | |
|---|---|---|
| CN | 101365532 A | 2/2009 |
| FR | 2782275 A1 | 2/2000 |

(Continued)

OTHER PUBLICATIONS

Aller Air Solutions. 1-6500 Series Filter Layout. Retrieved from www.allerairsolutions.com (2010).

(Continued)

*Primary Examiner* — Robert Clemente
(74) *Attorney, Agent, or Firm* — Caesar Rivise, PC

(57) ABSTRACT

Purified air is provided, having a TVOC content of from less than 5 ppb to about 500 ppb, a Biologicals content of from less than 1 $CFU/M^3$ to 150 $CFU/M^3$ and a Particulate content of from about 1,000 0.3 μm particles per $ft^3$ to about 50,000 0.3 μm particles per $ft^3$, or from about 600 0.5 μm particles per $ft^3$ to about 500,000 0.5 μm particles per $ft^3$.

12 Claims, 2 Drawing Sheets

(56) References Cited

U.S. PATENT DOCUMENTS

| | | |
|---|---|---|
| 6,843,818 B1 | 1/2005 | Cecchi |
| 7,132,003 B2 | 11/2006 | Hirayama et al. |
| 7,175,814 B2 | 2/2007 | Dionisio |
| 7,207,671 B2 | 4/2007 | Morris et al. |
| 7,326,387 B2 | 2/2008 | Arts et al. |
| 7,364,605 B2 | 4/2008 | Yuen |
| 7,416,588 B2 | 8/2008 | Burrows et al. |
| 7,449,053 B2 | 11/2008 | Hallam |
| 7,531,141 B2 | 5/2009 | Descotes et al. |
| 7,824,469 B2 | 11/2010 | Chan et al. |
| 8,668,883 B2 | 3/2014 | Garner |
| 2003/0198568 A1 | 10/2003 | Fencl |
| 2005/0053515 A1 | 3/2005 | Yates et al. |
| 2005/0173352 A1* | 8/2005 | Burrows ............ A61L 2/10 96/224 |
| 2006/0182672 A1* | 8/2006 | Hallam ............ A61L 9/015 422/186.07 |
| 2007/0041882 A1 | 2/2007 | Roseberry et al. |
| 2007/0056256 A1* | 3/2007 | Tepper ............ A61L 9/16 55/527 |
| 2007/0101867 A1 | 5/2007 | Hunter et al. |
| 2007/0251812 A1 | 11/2007 | Hayman |
| 2008/0019861 A1 | 1/2008 | Silderhuis |
| 2008/0213873 A1 | 9/2008 | Murray et al. |
| 2010/0009443 A1 | 1/2010 | Skinn |
| 2010/0196223 A1 | 8/2010 | Hay et al. |
| 2011/0120313 A1 | 5/2011 | Cho et al. |
| 2011/0171094 A1 | 7/2011 | Zahedi |
| 2011/0232481 A1 | 9/2011 | Worrilow |
| 2012/0024154 A1 | 2/2012 | Augustine et al. |
| 2012/0031271 A1 | 2/2012 | Haslebacher |
| 2012/0067215 A1 | 3/2012 | Lindahl et al. |
| 2012/0283508 A1 | 11/2012 | Worrilow |
| 2012/0318147 A1 | 12/2012 | Gates et al. |
| 2013/0149200 A1 | 6/2013 | Hong |

FOREIGN PATENT DOCUMENTS

| | | |
|---|---|---|
| WO | 2006128453 A1 | 12/2006 |
| WO | 2007116130 A1 | 10/2007 |
| WO | 2007136721 A2 | 11/2007 |
| WO | 2009120166 A1 | 10/2009 |

OTHER PUBLICATIONS

Cleanroom Technology. "A healthier air supply", Retrieved from www.cleanroom-technology.co.uk (2010).
Codaair. "The ultimate in air purification technology", Retrieved from www.codaair.com (2012).
English language abstract for FR 2782275 A1, p. 1 of FR 2782275 A1 (2000).
Enmet Corporation. "A definition of 'air' and the technical considerations in the production of compressed air for human respiration", Retrieved from www.enmet.com/pdf/Air-9515_Enmet.pdf (2015).
Freshlight Advanced Ultraviolet Technology. "FreshLight Air Sales Manual". Received by Applicant on May 2, 2013.
GENX. CodaTower product page on genX website. Retrieved on Nov. 10, 2011.
GENX. Homepage of genX website. Retrieved on Nov. 10, 2011.
International Air Filtration Corporation. "Always fresh systems" (2003).
International Air Filtration Corporation. "IAF negative air machine mold sterilization conversion kit". Retrieved from www.iafcleanair.com (2003).
International Standard. "Cleanrooms and associated controlled environments—part 1: classification of air cleanliness". First Edition (1999).
International Standard. "Cleanrooms and associated controlled environments—part 8: classification of airborne molecular contamination", First Edition (2006).
International Technology Roadmap for Semiconductors. "Yield Enhancement", 2011 Edition (2011).
Joyce et al. "Gas-phase contamination control for semiconductor clean rooms", Ashrae Journal, pp. 46-49 (1998).
Lifeaire Systems, LLC. "Aire-IVF system clinical outcome data", Retrieved from www.lifeaire.com/assets/ClinicalOutcomes-Eng.pdf on Feb. 3, 2015.
McMaster-Carr. "Portable heavy duty air cleaners". Retrieved from www.mcmaster.com on Oct. 3, 2012.
National Air Filtration Association. "NAFA user's guide for ANSI/ASHRAE 52.2", Retrieved from www.nafahq.org/LibraryFiles/Articles/Article006.htm (1999).
RX4CLEANAIR. "Whole-house duct mount HEPA air cleaner with ultraviolet light & photo catalytic filter". Retrieved from www.RX4CleanAirLLC.com (2009).
Sparks Technology, Inc. "Three stage commercial odor removal module" (2001).
Takahashi. "Airborne fungal colony-forming units in outdoor and indoor environments in Yokohama, Japan", Mycopathologia 139, pp. 23-33 (1997).
U.S. Department of Health and Human Services. "Guidance for industry: sterile drug products produced by aseptic processing—current good manufacturing practice". Pharmaceutical CGMPs (2004).
Worrilow. "IVF laboratories and UVC ionizing radiation". Ashrae IAQ Applications. Retrieved from www.ashrae.org (2008).
Zandair. "Zand-Air PCOC 3". Retrieved from www.zandair.com/zand-air-pcoc3 (2015).
Zandair. "zIVF-AIRe 100C Clean Air—Air filtration / purification systems photo-catalytic air purification for the IVF laboratory: FDA registered—zIVF-AIRe 100C FDA 510(k) # KO41952 for use in IVF laboratories". Retrieved from www.zandair.com/air-purification-filter-ivf-air.html on Jul. 5, 2008.
Notice of First Office Action for Chinese Application No. 201180016138.5 mailed Mar. 5, 2014.
International Search Report for PCT/US2011/029567 dated Jun. 30, 2011.
International Search Report for PCT/US2013/051057 dated Nov. 21, 2013.

* cited by examiner

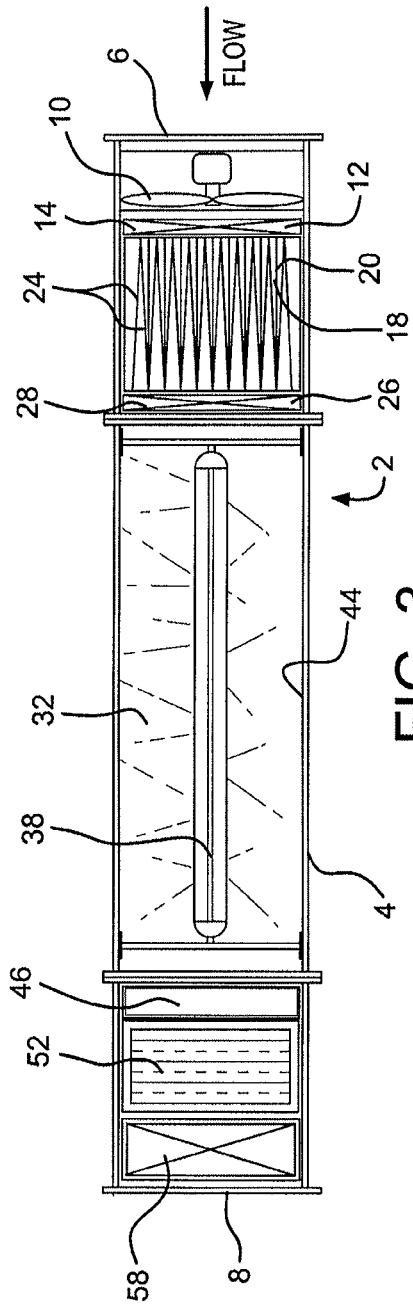
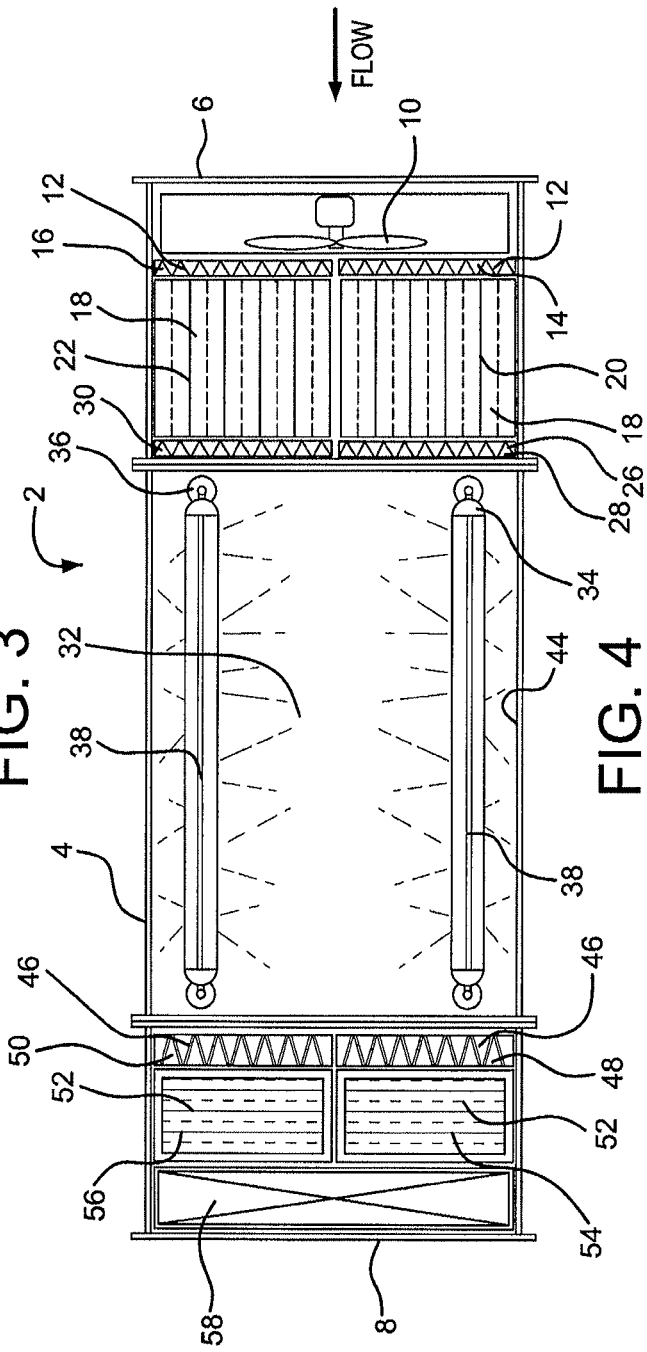

PURIFIED AIR AND METHODS OF MAKING AND USING THE SAME

This is a divisional application of U. S. patent application Ser. No. 13/554,366 which is a continuation-in-part of U.S. patent application Ser. No. 13/244,973, filed on Sep. 26, 2011, which is a continuation of U.S. patent application Ser. No. 12/732,246, filed on Mar. 26, 2010. International Application No. PCT/US2011/029567, filed on Mar. 23, 2011, claims priority to U.S. patent application Ser. No. 12/732, 246.

BACKGROUND OF THE INVENTION

1. Field of Invention

This invention relates to devices and methods for the filtration and purification of air. More particularly, this invention relates to air purifiers capable of providing a level of air quality suitable for environments that are highly sensitive to airborne contaminants, e.g., in vitro fertilization laboratories or other medical environments. Further, the invention may be adapted for use in any substantially enclosed environment, including, but not limited to, homes, residential buildings, commercial buildings, hotels, cars, buses, trains, airplanes, cruise ships, educational facilities, offices, and government buildings. The invention may also have applications in, e.g., national security, defense, or airline industries.

2. Description of Related Art

In vitro fertilization ("IVF") is a procedure whereby egg cells are fertilized by sperm in a laboratory environment, instead of in the womb. If an egg cell is successfully fertilized, it may be transferred into the uterus of a patient wishing to become pregnant.

IVF may be an effective option for patients suffering from infertility, especially where other methods of assisted reproduction have failed. However, IVF is very expensive and is not typically covered by medical insurance. In 2009, the cost of a single cycle of IVF was approximately $10,000 to $15,000 in the United States. It is financially prohibitive for most people to undergo multiple rounds of IVF. It is therefore imperative that conditions for successful pre-implantation embryogenesis are optimized, in order to maximize the likelihood of success.

One extremely important factor contributing to the likelihood of successful pre-implantation embryogenesis is the air quality of the IVF laboratory. Gametes and embryos grown in vitro are highly sensitive to environmental influences. Human embryos have no means of protection or filtration against environmental toxins and pathogens. They are completely at the mercy of their environment. The incubators which house the human embryos often consist of a significant percentage of room air. Although airborne contaminants can adversely affect embryogenesis, surprisingly little emphasis has been placed on optimizing laboratory air quality during the last three decades in which IVF has been available as a treatment for infertility.

Existing filtration devices have been found insufficient to optimize air quality to truly acceptable levels for IVF. For example, it has been found that laboratory air that had been filtered with only high efficiency particulate air ("HEPA") filters was actually of lesser quality than outside air. Additionally, some filters produce by-products or other contaminants that actually detract from the quality of the air in an IVF laboratory. For example, carbon filters can create carbon dusting that is harmful to the IVF process. This is not to say, however, that carbon filters or HEPA filters should not be used to treat air supplied to an IVF laboratory. On the contrary, it is preferred that carbon filters, HEPA filters, or their respective equivalents, are included among filtration media used to treat air supplied to an IVF laboratory. Attaining optimal air quality in an IVF laboratory or other substantially enclosed space requires proper selection, combination and sequencing of various filtration media.

BRIEF SUMMARY OF THE INVENTION

Accordingly, air characterized by very high purity and methods of making and using such air, are provided.

In one aspect of the present invention, air is provided, characterized by a TVOC content of from less than 5 ppb to about 500 ppb, a Biologicals content of from less than 1 $CFU/M^3$ to 150 $CFU/M^3$ and a Particulate content of from about 1,000 0.3 μm particles per $ft^3$ to about 50,000 0.3 μm particles per $ft^3$, or from about 600 0.5 μm particles per $ft^3$ to about 500,000 0.5 μm particles per $ft^3$.

Another aspect of the present invention is a method of achieving an IVF clinical pregnancy rate of at least 50%. The method includes performing multiple IVF cycles in an IVF laboratory having air characterized by a TVOC content of from less than 5 ppb to about 500 ppb, a Biologicals content of from less than 1 $CFU/M^3$ to 150 $CFU/M^3$ and a Particulate content of from about 1,000 0.3 μm particles per $ft^3$ to about 50,000 0.3 μm particles per $ft^3$, or from about 600 0.5 μm particles per $ft^3$ to about 500,000 0.5 μm particles per $ft^3$.

Another aspect of the present invention is a method of purifying air, including providing an air flow path through a housing for the flow of air in a downstream direction, filtering the air through oxidizing and adsorbing VOC pre-filtration within the housing, filtering the air through UV filtration within the housing, downstream from the oxidizing and adsorbing VOC pre-filtration and filtering the air through final particulate filtration within the housing, downstream from the UV filtration.

BRIEF DESCRIPTION OF SEVERAL VIEWS OF THE DRAWINGS

The invention will be described in conjunction with the following drawings in which like reference numerals designate like elements and wherein:

FIG. 3 is an internal view of the air purifier along the plane defined by section line A-A of FIG. 1.

FIG. 4 is an internal view of the air purifier along the plane defined by section line B-B of FIG. 2.

DETAILED DESCRIPTION OF THE INVENTION

Figure 1:
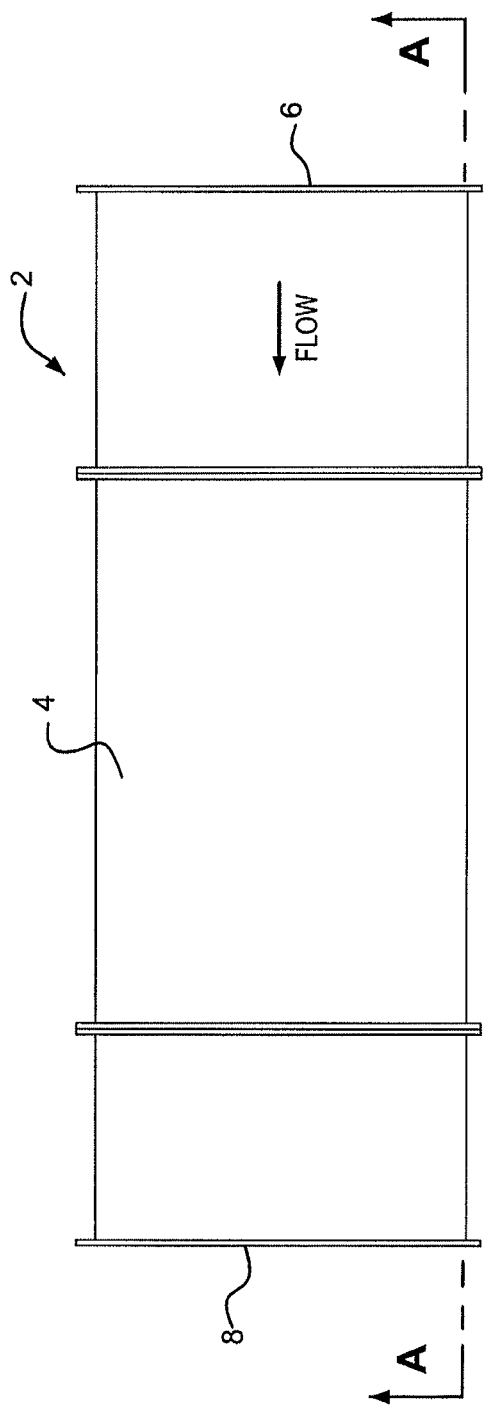
FIG. 1 is a top view of an air purifier according to the present invention.
Figure 2:
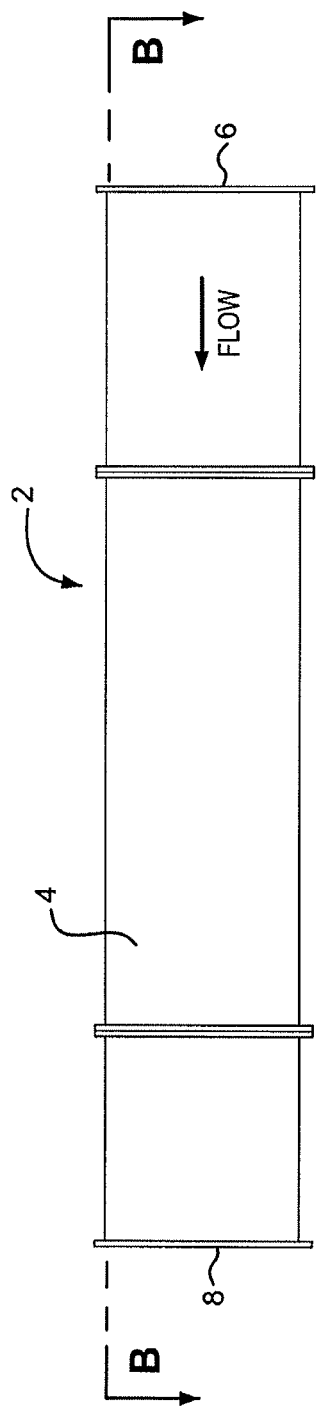
FIG. 2 is a side view of an air purifier according to the present invention.

Referring now in detail to the various figures of the drawings wherein like reference numerals refer to like parts, there are shown in FIGS. 1 and 2 top and side views, respectively, of an air purifier 2 according to the present invention. As illustrated, the air purifier 2 includes a substantially rectangular cuboid housing 4 having an inlet 6 for receiving air and an outlet 8 for exhausting air. The term "air" as used herein broadly refers to a gas or gaseous mixture that may be safely breathed by mammals and/or that can serve as a source gas or gaseous mixture towards an IVF laboratory. The housing 4 provides an air flow path for the flow of air in a downstream direction, i.e., from the inlet 6 towards the outlet 8. The term "housing" as used herein refers to any conduit, chamber and/or enclosure, or a plurality of conduits, chambers and/or enclosures coupled to one another, providing an air flow path within. Thus, the "housing" could include, e.g., ductwork of an existing heating, ventilating and air conditioning ("HVAC") system or air handling unit ("AHU").

Although the housing 4 is preferably substantially rectangular cuboid, as shown in FIGS. 1 and 2, it need not be limited to any particular shape. Moreover, it may include inner curves, bends and/or other contours, whereby the air flow path would follow such curves, bends and/or other contours. Preferably, however, the air flow path is substantially straight, as it is in the embodiment of the housing 4 shown in FIGS. 1 and 2.

The air purifier 2 is preferably adapted to be installed into an existing HVAC system or AHU. In an alternative embodiment, an air purifier according to the present invention may function as a stand-alone unit, i.e., one that is not part of an HVAC system or AHU. An exemplary housing 4 may be a substantially rectangular cuboid having dimensions of approximately 11 ft. long by 4 ft. wide by 2 ft. high. Such dimensions would diffuse or spread out the air through the air purifier 2 so as to provide sufficient resonance time for the air through each of the filtration media discussed infra. A skilled artisan understands, however, that the foregoing exemplary shape and size parameters are merely illustrative, and may be changed, even substantially, depending on the circumstances or application. For example, in some applications, the air purifier 2 may be about 6 ft. long.

Referring now to FIG. 3, there is shown an internal view of the air purifier 2 along the plane defined by section line A-A of FIG. 1. In FIG. 4, there is shown an internal view of the air purifier 2 along the plane defined by section line B-B of FIG. 2.

To obtain optimal air quality, e.g., suitable for an IVF laboratory, the air that is treated by the air purifier 2 should be pre-conditioned and stable, i.e., moderate both in terms of temperature and humidity. Ideally, the air that is treated by the air purifier 2 should have a temperature of between about 68° F. and 75° F., and a humidity of between about 45% and 55%. Additionally, the air flow rate through the air purifier 2 should preferably be about 250 ft./min. and below 2000 CFM. This preferred flow rate is intended to provide sufficient resonance time for the air through each of the filtration media discussed infra. The term "filtration" as used herein, broadly covers one or more devices that treat air, such as by trapping, removing, deactivating and/or destroying contaminants therefrom.

In order to provide an adequate air flow rate through the air purifier 2, it may be helpful (although not always necessary) to include a booster fan 10 downstream from the inlet 6. The booster fan 10 may be coupled to a control system (not shown) that measures the air flow rate and triggers the booster fan 10 as needed, to maintain the desired air flow rate. In an alternative embodiment (not shown), a booster fan may not be included, and adequate air flow rate may be provided and maintained by other means, e.g., a blower in an HVAC system or AHU into which the air purifier 2 is installed.

Downstream from the inlet 6 is particulate pre-filtration 12 for the trapping of airborne particulate. The particulate pre-filtration 12 is preferably about 2 inches thick in one embodiment, and includes left and right pleated particulate pre-filters 14, 16. The particulate pre-filters 14, 16 trap gross particulate (e.g., dust and bugs) from the outside air before that air reaches the other filtration media in the air purifier 2 discussed infra. Suitable filters for the particulate pre-filtration 12 are those having a Minimum Efficiency Reporting Value ("MERV") of 5 to 13 with an Average ASHRAE Dust Spot Efficiency (Standard 52.1) of 20% to 80%. Particularly preferred filters for the particulate pre-filtration 12 are pleated filters having a MERV of 7 to 8, with an Average ASHRAE Dust Spot Efficiency (Standard 52.1) of 30% to 45%.

Proper particulate pre-filter selection should be guided by the need to trap gross-particulate without unduly affecting the air flow rate through the air purifier 2. The particular type of particulate pre-filter(s) selected for particulate pre-filtration depends on various factors, including outside air quality. It is preferred that the particulate pre-filtration 12 is located immediately upstream from the additional filtration media discussed infra, as shown in FIGS. 3 and 4. Alternatively (or in addition), however, particulate pre-filtration may be located further upstream, e.g., in upstream ductwork of an HVAC system or AHU into which the air purifier 2 is installed.

Downstream from the particulate pre-filtration 12 is volatile organic compound ("VOC") pre-filtration 18. Once air passes through the particulate pre-filtration 12, the air is effectively free of gross particulate that would otherwise diminish the efficacy and useful life of the VOC pre-filtration 18. VOC pre-filtration ideally includes adsorption media, such as carbon, as well as oxidation media, such as potassium permanganate ("$KMnO_4$") or a photocatalytic oxidizer. A particularly preferred type of carbon is virgin coconut shell. In a preferred embodiment, the VOC pre-filtration 18 is a carbon and $KMnO_4$ blend, e.g., in a 50/50 proportion. In some embodiments, the blend may include additional elements, such as natural zeolite. The proportion of the blend may vary depending on the types and levels of VOCs present in the source air. Ideally, the source air would be tested for VOCs, and, based on test results, a custom blend would be prepared to maximize VOC removal in a given environment. In an alternative embodiment of the VOC pre-filtration (not shown), separate (i.e., non-blended) carbon and $KMnO_4$ filters are used.

The embodiment of the VOC pre-filtration 18 shown in FIGS. 3 and 4 includes a total of twenty stacked filter trays 20, 22, whereby ten such trays 20 are on the left side of the housing 4 and ten such trays 22 are directly adjacent, to the right. The length of the trays, i.e., the longitudinal distance over which the air flows, is preferably about 17 inches in one embodiment, though it may be shorter or longer. Each tray 20, 22 includes two blended carbon and $KMnO_4$ filters 24, arranged in a V-bank along a vertical plane (e.g., the plane of FIG. 3). The V-bank arrangement increases the surface area of the filters 24 over which air must travel, thereby enhancing the effectiveness of the VOC pre-filtration 18. Once air passes through the VOC pre-filtration 18, the VOC load of the air is effectively reduced.

Downstream from the VOC pre-filtration 18 is particulate post-filtration 26 for the trapping of airborne particulate, e.g., particulate generated by the VOC pre-filtration 18 (such as carbon dusting). The particulate post-filtration 26 includes left and right pleated particulate post-filters 28, 30. The filters used in the particulate post-filtration 26 may be identical or similar to those used in the particulate pre-filtration 12, discussed supra. While particulate post filtration 26 downstream from the VOC pre-filtration 18 is preferred, it may not be necessary in all applications. For example, if the VOC pre-filtration is of a type that does not generate air-borne particulate, such as bonded carbon, particulate post-filtration may be optional.

Downstream from the particulate post-filtration 26 is ultraviolet ("UV") filtration 32 which destroys airborne biological contaminants and, in some embodiments, degrades chemical contaminants. Whether or not particulate post-filtration 26 is used, the air reaching the UV filtration 32 should be effectively free of gross particulate and contain dramatically reduced levels of VOCs so as not to diminish the efficacy of the UV filtration 32.

The UV filtration may include one or more UV sources, although a plurality of UV sources is preferred. It is further preferred that these UV sources are UVC sources, capable of generating UV radiation at a wavelength varying from 220 nm to 288 nm. Most preferably, the UVC sources are capable of generating UV radiation at a wavelength of 260 nm, however commercially available UVC sources capable of generating UV radiation at a wavelength of 254 nm are adequate. In an alternative embodiment described in U.S. Pat. No. 5,833,740 (Brain), which is incorporated herein by reference in its entirety, the UV filtration includes at least one vacuum UV source, capable of generating UV radiation at a wavelength varying from 170 nm to 220 nm (preferably 185 nm) and at least one UVC source, capable of generating UV radiation at a wavelength varying from 220 nm to 288 nm (preferably 260 nm). In that embodiment, the UVC source is preferably downstream from the vacuum UV source. When operating, the vacuum UV source breaks oxygen molecules into mono-atomic oxygen which then reacts with chemical contaminants present in the air and then degrades them by successive oxidation to odorless and inoffensive byproducts. The UVC source kills biological contaminants present in the air by irradiation and degrades residual ozone produced by the vacuum UV source into molecular oxygen.

Particularly preferred UV filtration 32 shown in FIGS. 3 and 4 is the "UV Bio-wall" made by Sanuvox. Alternatively, the "Bio 30GX," which is also made by Sanuvox, is a preferred type of UV filtration. The UV filtration 32 includes a pair of fixtures 34, 36 each of which has five UV lamps 38 (not all five of which are visible in the Figures). The UV lamps 38 are preferably about 60 inches long and extend longitudinally through the housing 4 so as to maximize exposure time of the air to UV radiation. In one embodiment, the UV lamps are UVC sources, providing UV radiation within the UVC wavelength parameters discussed supra. In an alternative embodiment, described in U.S. Pat. No. 5,833,740 (Brais), each lamp 38 is dual-zoned, having an upstream vacuum UV source and a downstream UVC source. In that alternative embodiment, the upstream vacuum UV source may, e.g., be a high intensity mercury vapor lamp capable of generating UV radiation having a wavelength in a range of about 170 nm to about 220 nm, and the downstream UVC source may, e.g., be a low intensity mercury vapor lamp capable of generating radiation having a wavelength in a range of about 220 nm to about 288 nm. The interior 44 of the housing 4 encasing the UV filtration 32 is highly reflective, with a preferable coefficient of reflection of at least 60%, so as to enhance the effectiveness of the lamps 38.

The kill rate of biological contaminants is a function of the intensity of UVC radiation produced by the UV filtration 32 and reflected by the interior 44 of the housing 4, as well as the exposure time of such contaminants to the UVC radiation. Thus, the higher the intensity of the UVC radiation and the longer the exposure time of such contaminants to the UVC radiation, the greater is the level of sterilization achieved. Depending on factors such as the desired level of sterilization, the amount of space available to house UV filtration, and costs of operating and maintaining UV filtration, the desired total UVC output of the UV filtration 32 may vary. In one actual embodiment, it was found that a total UVC output ranging from about 33,464 $\mu J/cm^2$ to about 90,165 $\mu J/cm^2$, with an average total UVC output of about 43,771 $\mu J/cm^2$, provided a desired level of sterilization, given practical constraints of cost and space. Such total UVC output killed 100% of numerous biological contaminants including, but not limited to smallpox, flu, tuberculosis, anthrax and H1N1 virus.

The UV filtration 32 contained within the housing 4 is likely not visible to a user of the air purifier 2 when in use, because direct UV exposure is harmful to humans. Thus, a user cannot ascertain visually (i.e., by simply looking at the air purifier 2 itself) whether the lamps 38 are operating at a given time. It cannot be assumed that the air purifier 2 is effectively destroying air-borne biological and chemical contaminants, without knowing for sure that the UV filtration is operating properly. Accordingly, it is preferred that the present invention include sensors and a monitor (not shown) to detect and indicate, respectively, how much time each UV lamp 38 has been in use and whether each lamp 38 is operating at a given time. The monitor may include, e.g., a scrolling digital clock, which indicates the length of time each lamp 38 has been operating. These sensors and monitor would indicate to a user when it is time to replace any of the lamps 38.

As a general matter, moisture within the housing 4 can foster the growth of biological contaminants. Accordingly, it is preferable to include a UVC source in the vicinity of areas in which moisture is generated or gathers. For example, upstream from the particulate pre-filtration 12 may be one or more cooling coils (not shown) that help to ensure that the air which is treated by the air purifier 2 is moderate in terms of temperature. Such cooling coils tend to generate moisture. It is therefore preferable to include a UVC source adjacent to such cooling coils. Similarly, it may be appropriate to include a UVC source immediately upstream from a filter/diffuser (not shown) from which the air enters into a substantially enclosed space, e.g., an IVF laboratory or other room, after leaving the air purifier 2.

Downstream from the UV filtration 32 is VOC post-filtration 46, which capture, e.g., VOC by-products of the irradiation from the UV filtration 32. Possible embodiments of the VOC post-filtration 46 include any of those discussed supra regarding the VOC pre-filtration 18. The VOC post-filtration 46 shown in FIGS. 3 and 4 includes left and right VOC post-filters 48, 50 that are arranged in a V-bank along a horizontal plane (e.g., the plane of FIG. 4). The VOC post-filters 48, 50, like their upstream counterparts, are preferably blended carbon and $KMnO_4$. Although VOC post-filtration 46 is preferred, in some applications, it may not be required and may thus be omitted.

Gametes and the human embryo are highly sensitive to VOCs, even in amounts considered negligible in other applications. It is therefore essential that the VOC filtration (both pre-filtration 18 and post-filtration 46) operates effectively to remove VOCs from air that is fed into an environment in which IVF is being conducted. Accordingly, one or more sensors for detecting VOC levels (not shown), preferably in real time, may be placed in an IVF laboratory and coupled to a monitor (not shown) to indicate the VOC levels in the laboratory at a given time. With such in-room VOC detection, a user of the air purifier 2 would know when it is time to replace the VOC pre-filtration 18 and post filtration 46, and/or whether an alternative type or blend of VOC filters would be more suitable. While in-room VOC detection is particularly useful in an IVF laboratory, it may be helpful in any environment requiring low VOC levels.

Downstream from the VOC post-filtration 46 is final particulate filtration 52, which traps substantially all remaining particulate in the air before the air exits the outlet 8. Final particulate filtration 52 preferably includes one or more filters capable of trapping fine airborne particulate, e.g., filters having a MERV of 13 or greater with an average ASHRAE Dust Spot Efficiency (Std. 52.1) of 80% or greater. More preferably, such filters have a MERV of 16 or greater with an average ASHRAE Dust Spot Efficiency (Std. 52.1) of 95% or greater. Most preferably, such filters have a MERV of 17 or greater with an average ASHRAE Dust Spot Efficiency (Std. 52.1) of 99.97%, as do high efficiency particulate air ("HEPA") filters. Alternatively, ultra low particulate air ("ULPA") filters may be suitable. The choice of filter(s) for final particulate filtration should be guided by the potentially competing needs of maintaining an optimal air flow rate and effectively removing particulate from the air.

The final particulate filtration 52 of FIGS. 3 and 4 includes left and right 12-inch thick HEPA filters 54, 56. Preferably, magnehelic gauges (not shown) are placed both upstream and downstream from the HEPA filters 54, 56 to measure the pressure drop across those filters. The degree of pressure drop will assist in the identification of the proper time in which to change the HEPA filters 54, 56, or other filters used for final particulate filtration.

Downstream from the final particulate filtration 52, is an atomizing humidifier 58. The humidifier 58 may or may not be necessary, depending on the needs of the facility in which the air purifier 2 is being used. However, if a humidifier 52 is needed, it should be placed downstream from the final particulate filtration 52 so that the moisture does not adversely affect the performance of the VOC post-filters 48, 50, the HEPA filters 54, 56, or other filters used for final particulate filtration. Humidified air can contain and support the growth of biological contaminants. Accordingly, if a humidifier 58 is used, an additional UVC source (not shown) to destroy such contaminants should also be included. This additional UVC source should be downstream from the humidifier 58, preferably at the last point in ductwork before entry into a room served by the purified air.

An air purifier according to the present invention, such as that described in detail, supra, will produce air characterized by very high purity, suitable for airborne contaminant-sensitive environments such as IVF laboratories or other medical environments, for example. That said, an air purifier according to the present invention is not limited to IVF or other medical applications. It may be adapted for use in any substantially enclosed environment, including, but not limited to, homes, residential buildings, commercial buildings, hotels, cars, buses, trains, airplanes, cruise ships, educational facilities, offices, and government buildings. The invention may also have applications in, e.g., national security, defense, or airline industries. The desired purity of the air may vary depending on application and environment. An air purifier according to the present invention, such as that described in detail, supra, may be adapted accordingly to achieve a desired level of purity. The sequence and type of air filtration media in an air purifier according to the present invention provides air characterized by a purity that was unattainable with prior devices.

Accordingly, another aspect of the present invention includes purified air, such as that attainable using an air purifier as described herein. Ideally, such purified air would be characterized by a high level of purity as measured by three parameters: (a) "TVOC," i.e., total volatile organic compounds, measured in "ppb," or parts per billion; (b) "Biologicals," i.e., biological contaminants, including spores, measured in "$CFU/M^3$," or colony forming units per cubic meter; and (c) "Particulate," i.e., the number of particles per cubic foot having, e.g., nominal sizes of 0.3 µm or 0.5 µm.

TVOC measurements may be made, e.g., using GRAY WOLF SENSING SOLUTIONS, Model No. TG-502 Toxic Gas Probe with Photo Ionization Detector ("PID") sensors utilizing a 10.6 eV lamp calibrated to Isobutylene. The lowest detectable limit of TVOCs using the TG-502 Toxic Gas Probe is 5 ppb.

To ensure accuracy, measurements of Biologicals are preferably assessed using two complementary methods. According to a first method of measuring Biologicals, ambient air (i.e., the air being tested) is drawn over ALLER-GENCO D spore traps using a high volume vacuum pump calibrated to draw 15 liters of air per minute. This is done for 10 minutes, so that a total of 150 liters of air is drawn through the spore trap cassette. The traps are then examined by direct light microscopic observation to determine the identification of some select types of biological contaminants present in terms of $CFU/M^3$. According to a second method of measuring Biologicals, an ANDERSON N6 sampler is utilized to obtain culturable air samples (from the ambient air being tested) on three types of media: malt extract agar, cellulose agar and DG-18. The sampler is calibrated pre- and post-collection to draw a rate of 28.3 liters per minute for a sample time of 5 minutes. Using this second method of measuring Biologicals enables determination of the unique identification of any biological contaminant present in terms of $CFU/M^3$ due to the three different types of growth media.

The particulate measurements may be made, e.g., using a TSI AEROTRAK 9306 Handheld Particle Counter. The particle counter is preferably calibrated with NIST traceable PSL spheres using TSIs Classifier and Condensation Particle Counters, the recognized standard for particle measurements. The particle concentrations in the air are measured at nominal particle sizes of 0.3 µm, 0.5 µm, 1.0 µm, 3.0 µm, 5.0 µm, and 10.0 µm, per cubic foot ($ft^3$).

In a preferred embodiment, it is contemplated that purified air attainable using an air purifier as described herein, is characterized by: (a) a TVOC content of less than 5 ppb (or below detectable limits using the GRAY WOLF SENSING SOLUTIONS, Model No. TG-502 Toxic Gas Probe with PID sensors described supra, or another instrument with similar measurement capabilities and tolerances); (b) a Biologicals content of less than 1 $CFU/M^3$ (or below detectable limits using the methods of measuring Biologicals described supra, or other methods with similar measurement capabilities and tolerances); and (c) a particulate content of from about 1,000 0.3 µm particles per $ft^3$ of air to about 10,500 0.3 µm particles per $ft^3$ of air, or from about 600 0.5 µm particles per $ft^3$ of air to about 1,000 0.5 µm particles per $ft^3$ of air.

Depending on the application or environment, acceptable levels of TVOCs, Biologicals and particulates may vary. For example, in one embodiment, the purified air may be characterized by: (a) a TVOC content of from less than 5 ppb to about 500 ppb; (b) a Biologicals content of from less than 1 $CFU/M^3$ to 150 $CFU/M^3$; and (c) a particulate content of from about 1,000 0.3 µm particles per $ft^3$ of air to about 50,000 0.3 µm particles per $ft^3$ of air, or from about 600 0.5 µm particles per $ft^3$ of air to about 500,000 0.5 µm particles per $ft^3$ of air. More preferable particulate content is from about 1,000 0.3 µm particles per $ft^3$ of air to about 30,000 0.3 µm particles per $ft^3$ of air, or from about 600 0.5 µm particles per $ft^3$ of air to about 10,000 0.5 µm particles per $ft^3$ of air. Particularly preferred particulate content is from about 1,000 0.3 µm particles per $ft^3$ of air to about 10,500 0.3 µm particles per ft³ of air, or from about 600 0.5 μm particles per ft³ of air to about 1,000 0.5 μm particles per ft³ of air.

Another aspect of the invention includes providing purified air to an IVF laboratory to improve IVF clinical pregnancy rates and/or implantation rates. The clinical pregnancy rate refers to the presence of a fetal heart beat within an intrauterine sac. The implantation rate refers to the ability of a single embryo to implant within the uterus and develop a fetal heartbeat. A method of the present invention may comprise providing purified air, such as air as characterized supra, to an IVF laboratory, performing multiple cycles of IVF in the laboratory, and achieving a clinical pregnancy rate equal to or greater than 50% and/or an implantation rate of equal to or greater than 35% based on a minimum patient population of 20 patients. In one embodiment, it is contemplated that achievable clinical pregnancy rates would be from 50% to 70% and more preferably from 60% to 70%. In another embodiment, it is contemplated that achievable implantation rates would be from 35% to 40%.

Various aspects of the invention will be illustrated in more detail with reference to the following Examples, but it should be understood that the present invention is not deemed to be limited thereto.

EXAMPLES

Prior to the air purifier described herein, the national average for clinical pregnancy rates was approximately 38%. Couples often had to complete multiple cycles of IVF to conceive because the overall success rates were relatively low. As discussed supra, the cost of a single IVF cycle is high and multiple cycles are cost prohibitive to many. Accordingly, there has been a strong and long-felt need—essentially since the advent of IVF approximately 30 years ago—to significantly improve IVF clinical pregnancy rates in order to make IVF a more viable option for infertility patients.

Prior to invention of the air purifier described herein, the inventor found that IVF laboratory air quality was not conducive to the successful growth of an embryo, even if extant filtration systems were utilized. Extant air filtration systems did not deliver the air quality necessary to support the human embryo and thus did not noticeably improve IVF clinical outcomes. In addition, extant air filtration systems did not protect the IVF laboratory against varying concentrations of airborne contaminants from the outside or source air. For example, if a nearby road or roof was being tarred, the toxic chemicals released would potentially enter the source air and the IVF laboratory and thus, impact the developing embryos.

Below are examples of how the air purifier described herein provides significant improvements in the art, representing surprising and unexpected results and satisfaction of a long-felt and unmet need. The examples compare the air purifier described herein with extant air filtration systems, including the Coda® System and Zandair System. The Coda® System and Zandair System have been the primary air filtration systems used in IVF laboratories for at least the last ten years.

Example 1

An embodiment of the air purifier described herein was installed in an IVF laboratory beta site. Prior to that installation, the laboratory used two Coda® Systems. Each Coda® System included, from an upstream towards a downstream direction: (1) particulate filtration; (2) carbon and KMnO₄ filtration; and (3) HEPA filtration. Prior to installation of the aforementioned embodiment of the air purifier, clinical pregnancy rates at the laboratory were 36.4%, which is near the national average of about 38%. The embodiment of the air purifier described herein that was installed in the laboratory included, from an upstream towards a downstream direction: (1) particulate filtration (located upstream in the air handler unit); (2) carbon and KMnO₄ filtration; (3) UV filtration; (4) carbon and KMnO₄ filtration; and (5) HEPA filtration. After installation of the aforementioned embodiment of the air purifier, clinical pregnancy rates at the laboratory jumped to 67.4% based on a patient population of 191 patients—representing significant and surprising results in clinical outcomes and patient care.

"Before" and "after" IVF implantation rates at the laboratory were also measured. Prior to installation of the aforementioned embodiment of the air purifier, the implantation rate at the laboratory was 21% and the national average was 26.1%. After installation of the aforementioned embodiment of the air purifier, the implantation rate at the IVF laboratory beta site increased to 39% based on a patient population of 191 patients—representing significant and surprising results in clinical outcomes and patient care. The significant and surprising increase in implantation rates has allowed the program at the laboratory to return fewer embryos per patient thus reducing the chance of multiple pregnancies (e.g., twins, triplets, etc.) and improving the overall obstetrical outcome.

In sum, these significant improvements in both clinical pregnancy rates and implantation rates demonstrate that the aforementioned embodiment of the air purifier described herein achieved unexpected results relative to the closest prior art and satisfied a long-felt and unmet need.

Example 2

The following three charts provide data from independent third party testing of air quality in an IVF laboratory. Common to all three charts is the following terminology: (1) "Source Air"—the air going into an IVF laboratory prior to entering a respective filtration system; (2) "IVF Laboratory"—the ambient air within the IVF laboratory; (3) "TVOC"—total volatile organic compounds, measured in "ppb," or parts per billion; (4) "Biologicals"—biological contaminants, including spores, measured in "CFU/M³," or colony forming units per cubic meter; and (5) "Particulate"—the number of particles per cubic foot having nominal sizes of 0.3 μm and 0.5 μm. These measurements were made using measuring devices and techniques described supra.

CHART NO. 1

| | IVF Laboratory Using Two (2) CODA Air Filtration Systems | |
|---|---|---|
| | Source Air | IVF Laboratory |
| TVOC | 1324 ppb | 1372 ppb |
| Biologicals | 469 CFU/M³ | 1778 CFU/M³ |
| Particulate | 2,318,663 0.3 μm particles per ft³ | 11,642 0.3 μm particles per ft³ |
| | 1,874,789 0.5 μm particles per ft³ | 9,421 0.5 μm particles per ft³ |

Chart No. 1 compares the source air quality versus the IVF laboratory air quality where the IVF laboratory air had been subjected to two Coda® Systems, as they are described in Example 1, supra. As Chart No. 1 shows, the air in the IVF laboratory actually had higher levels of TVOC and biological contaminants (including spores) than did the source air. Only the levels of particulates dropped between the source air and the IVF laboratory air.

CHART NO. 2

IVF Laboratory
Using Three (3) Zandair Filtration Systems

|  | Source Air | IVF Laboratory |
|---|---|---|
| TVOC | 594 ppb | 1030 ppb |
| Biologicals | 28 CFU/$M^3$ | 113 CFU/$M^3$ |
| Particulate | 380,098 | 5,722 |
|  | 0.3 µm | 0.3 µm |
|  | particles per $ft^3$ | particles per $ft^3$ |
|  | 1,695,377 | 41,472 |
|  | 0.5 µm | 0.5 µm |
|  | particles per $ft^3$ | particles per $ft^3$ |

Chart No. 2 compares the source air quality versus the IVF laboratory air quality where the IVF laboratory air had been subjected to three Zandair Systems. Each Zandair System included, from an upstream towards a downstream direction: (1) carbon filtration; (2) HEPA filtration; and (3) photo-catalytic oxidation along with UV filtration. As Chart No. 2 shows, the air in the IVF laboratory actually had higher levels of TVOC and biological contaminants (including spores) than did the source air. Only the levels of particulates dropped between the source air and the IVF laboratory air.

CHART NO. 3

IVF Laboratory
Using a Single (1) Embodiment of
Applicant's Air Purifier Described Herein

|  | Source Air | IVF Laboratory |
|---|---|---|
| TVOC | 1400 ppb | Less than 5 ppb |
| Biologicals | 15,240 CFU/$M^3$ | Less than 1 CFU/$M^3$ |
| Particulate | 1,063,435 | 5,410 |
|  | 0.3 µm | 0.3 µm |
|  | particles per $ft^3$ | particles per $ft^3$ |
|  | 98,763 | 625 |
|  | 0.5 µm | 0.5 µm |
|  | particles per $ft^3$ | particles per $ft^3$ |

Chart No. 3 compares the source air quality versus the IVF laboratory air quality where the IVF laboratory air had been subjected to only a single embodiment of the air purifier described herein. The aforementioned embodiment of the air purifier included, from an upstream towards a downstream direction: (1) particulate filtration (located upstream in the air handler unit); (2) carbon/$KMnO_4$ filtration; (3) UV filtration; (4) carbon/$KMnO_4$ filtration; and (5) HEPA filtration. As shown in Chart No. 3, unlike the air quality results for the two Coda® Systems and the three Zandair Systems provided in Chart Nos. 1 and 2 respectively, the single aforementioned embodiment of the air purifier significantly improved air quality with respect to all three measured endpoints, i.e., (1) TVOC; (2) Biologicals; and (3) Particulate.

The Coda® System and Zandair System have been the primary air filtration systems used in IVF laboratories for at least the last ten years. The independent third party testing results provided in Chart Nos. 1, 2 and 3 demonstrate that the air purifier described herein provided markedly superior air purity compared to the primary air filtration systems used in IVF laboratories for at least the last ten years. The superior air purity generated by the air purifier described herein is surprising. Also surprising are the significantly improved clinical pregnancy rates and implantation rates described in Example 1, supra, resulting from the superior air purity generated by the air purifier described herein.

Taken together, Examples 1 and 2 demonstrate that performing IVF in ambient air that has been purified to levels disclosed herein for three parameters—TVOCs, Biologicals and Particulate—unexpectedly and significantly improve IVF clinical pregnancy rates and implantation rates. In addition, given that IVF has existed for approximately 30 years and that the Coda® System and Zandair System have been the primary air filtration systems used in IVF laboratories for at least the last ten years, there has been a long-felt and unmet need for an improved air purifier for, among other things, IVF applications. The air purifier described herein has satisfied that need.

Example 3

An embodiment of the air purifier described herein was installed in an IVF laboratory beta site. This embodiment included, from an upstream towards a downstream direction: (1) particulate filtration (located upstream in the air handler unit); (2) carbon and $KMnO_4$ filtration; (3) UV filtration; (4) carbon and $KMnO_4$ filtration; and (5) HEPA filtration.

A catastrophic load of VOCs was accidentally introduced into the building that housed the IVF laboratory. In particular, a contractor had poured floor sealant on a large floor surface area in a room just adjacent to the IVF laboratory. The floor sealant comprised 10% xylene and 40% acetone. Both xylene and acetone are highly embryotoxic. While staff outside of the IVF laboratory developed nausea and intense headaches from the fumes, the aforementioned embodiment of the air purifier protected the embryos and staff within the IVF laboratory. TVOC testing before and during the accident demonstrated that despite over 6000 ppb TVOCs immediately outside of the laboratory—an extremely high level—the TVOC levels did not change within the laboratory.

In sum, the significant and surprising results of Applicant's air purifier, as demonstrated in Examples 1, 2 and 3, were surprising and unexpected to the inventor and would be surprising and unexpected to persons of ordinary skill in the art. Those examples also help demonstrate how Applicant's air purifier has satisfied a long-felt and unmet need for an improved air purifier which allows for significantly improved clinical pregnancy rates and implantation rates.

While the invention has been described in detail and with reference to specific examples thereof, it will be apparent to one skilled in the art that various changes and modifications can be made therein without departing from the spirit and scope thereof.

The invention claimed is:

1. A method of performing in-vitro fertilization ("IVF"), the method comprising: providing purified air, wherein the purified air is characterized by:
    a. a TVOC content of from less than about 5 ppb to about 500 ppb;
    b. a Biologicals content of from less than about 1 CFU/$M^3$ to 150 CFU/$M^3$; and
    c. a Particulate content of from about 1,000 0.3 µm particles per $ft^3$ of air to about 30,000 0.3 µm particles per $ft^3$ of air, or from about 600 0.5 µm particles per $ft^3$ of air to about 10,000 0.5 µm particles per $ft^3$ of air, and performing at least one IVF procedure in said purified air.

2. The method of claim 1, wherein the at least one IVF procedure comprises a plurality of IVF procedures.

3. The method of claim 2, wherein the plurality of IVF procedures results in a clinical pregnancy rate of at least 50%.

4. The method of claim 2, wherein the plurality of IVF procedures results in a clinical pregnancy rate of from 50% to 70%.

5. The method of claim 2, wherein the plurality of IVF procedures results in a clinical pregnancy rate of from 50% to 65%.

6. The method of claim 2, wherein the plurality of IVF procedure results in a clinical pregnancy rate of from 55% to 70%.

7. The method of claim 2, wherein the plurality of IVF procedures results in a clinical pregnancy rate of from 55% to 65%.

8. A method of achieving an IVF clinical pregnancy rate of at least 50%, the method comprising: performing multiple IVF cycles in purified air characterized by:
   a. a TVOC content of less than about 5 ppb;
   b. a Biologicals content of less than about 1 $CFU/M^3$; and
   c. a Particulate content from about 1,000 0.3 μm particles per $ft^3$ to about 10,500 0.3 μm particles per $ft^3$, or from about 600 0.5 μm particles per $ft^3$ to about 1,000 0.5 μm particles per $ft^3$,
   thereby achieving an IVF clinical pregnancy rate of at least 50%.

9. The method of claim 8, wherein the IVF clinical pregnancy rate is from 50% to 70%.

10. The method of claim 8, wherein the IVF clinical pregnancy rate is from 50% to 65%.

11. The method of claim 8, wherein the IVF clinical pregnancy rate is from 55% to 70%.

12. The method of claim 8, wherein the IVF clinical pregnancy rate is from 55% to 65%.

* * * * *